US00PP30552P3

(12) United States Plant Patent
Brewer et al.

(10) Patent No.: US PP30,552 P3
(45) Date of Patent: Jun. 4, 2019

(54) PEAR TREE NAMED 'PREMP009'

(50) Latin Name: ***Pyrus communis* x *Pyrus pyrifolia* x *Pyrus* X *bretschneideri***
Varietal Denomination: PremP009

(71) Applicants: Lester Brewer, Auckland (NZ); Richard Volz, Auckland (NZ)

(72) Inventors: Lester Brewer, Auckland (NZ); Richard Volz, Auckland (NZ)

(73) Assignee: Prevar Limited, Hastings (NZ)

( * ) Notice: Subject to any disclaimer, the term of this patent is extended or adjusted under 35 U.S.C. 154(b) by 499 days.

(21) Appl. No.: 14/544,845

(22) Filed: Feb. 24, 2015

(65) Prior Publication Data

US 2015/0245551 P1 Aug. 27, 2015

Related U.S. Application Data

(60) Provisional application No. 61/966,638, filed on Feb. 26, 2014.

(51) Int. Cl.
*A01H 5/08* (2018.01)

(52) U.S. Cl.
USPC ..... Plt./176
CPC ..... *A01H 5/08* (2013.01)

(58) Field of Classification Search
USPC ..... Plt./176
CPC ..... A01H 5/0881
See application file for complete search history.

(56) References Cited

PUBLICATIONS

GTITM UPOVROM Citation for 'Premp009' as per NZ PBR PER028; Jan. 27, 2014; 1 page.*

* cited by examiner

*Primary Examiner* — Kent L Bell
(74) *Attorney, Agent, or Firm* — Michelle Bos Legal LLC

(57) ABSTRACT

A new and distinct pear tree named 'PremP009' is disclosed. The new pear is notable for its attractive appearance, superb texture, improved flavor and long shelf life.

2 Drawing Sheets

Latin name of the genus and species of the plant claimed: *Pyrus communis* x *Pyrus pyrifolia* x *Pyrus* X *bretschneideri*.
Variety denomination: 'PremP009'.

BRIEF DESCRIPTION OF THE PHOTOGRAPHS

The photographs were taken in 2013 at Hawkes Bay, New Zealand

BRIEF DESCRIPTION OF THE VARIETY

Figure 1:
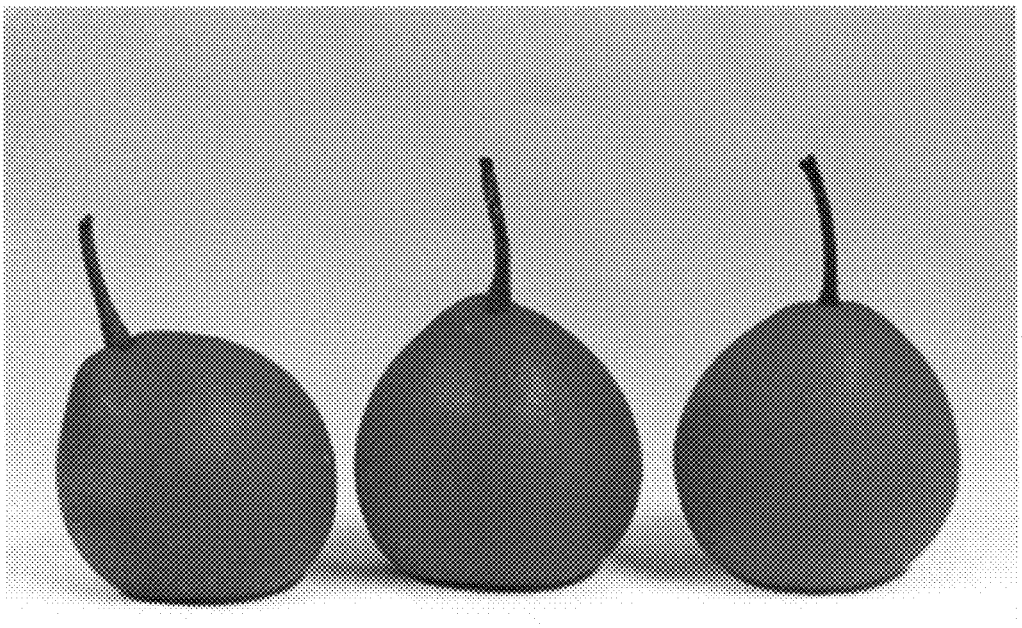
FIG. 1 shows fruit of the 'PremP009' variety.
Figure 2:
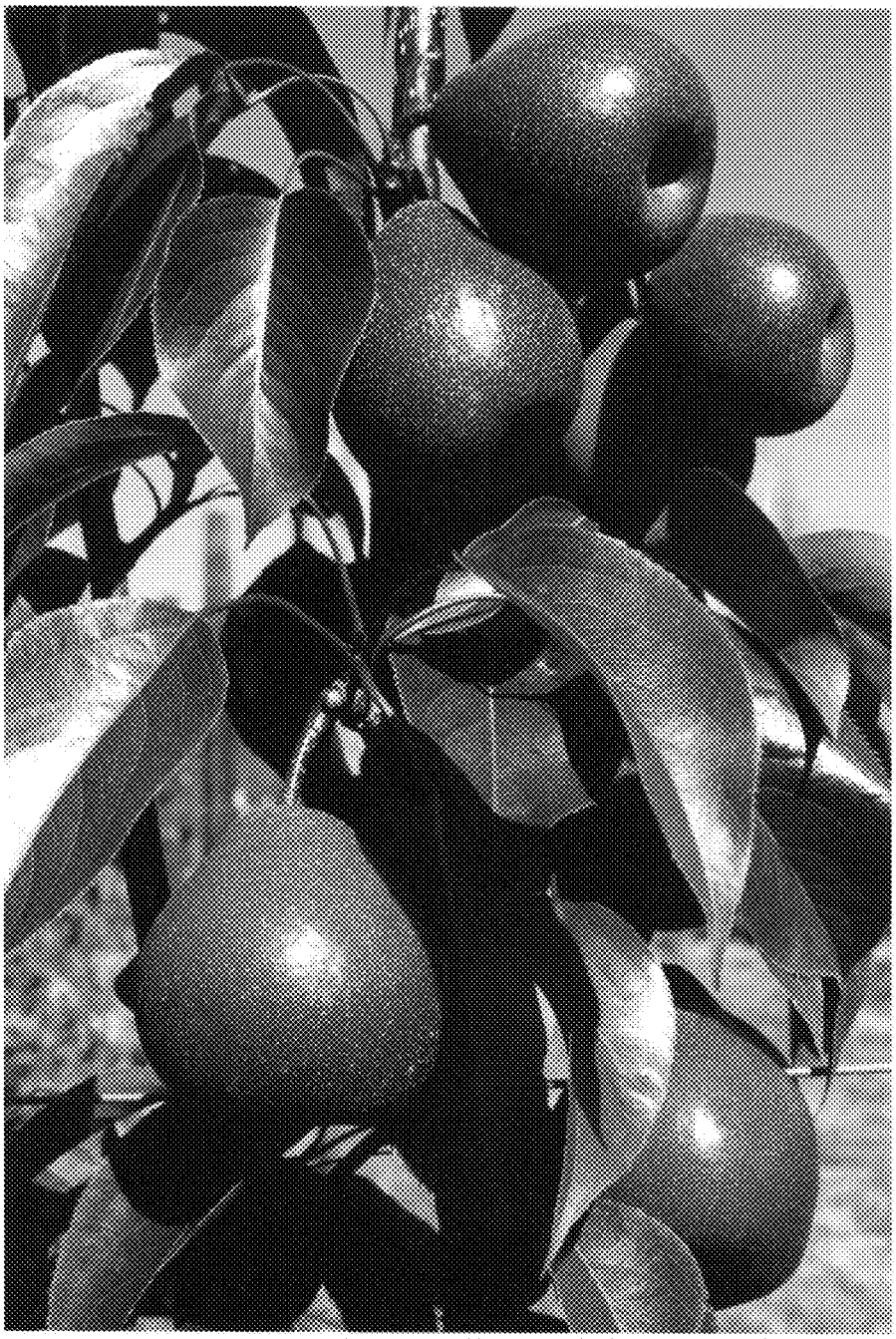
FIG. 2 shows fruit and leaves on a four-year-old 'PremP009' tree.

The new variety of pear tree 'PremP009' was created in the course of a planned breeding program carried out in Havelock North, New Zealand. 'PremP009' originated as a result of a controlled cross of 'P128R068T003' (seed parent, not patented) and 'P204R135T058' (pollen parent, not patented). 'PremP009' was selected in 2005 as a single plant from among a population of seedlings derived from the parents, and was selected for its fruit, which exhibits an attractive intense dark red skin color and unique appearance, superb texture and flavor, and long shelf life. 'PremP009' has a red skin color, which differs from the yellow skin color of its parent variety 'P128R068T003'. 'PremP009' also has a medium to long period of postharvest storage compared to the short period of storage available to its pollen parent, 'P204R135T058'. Table 1 compares 'PremP009' to a similar variety, 'PremP109' (U.S. Plant Pat. No. 24,408).

TABLE 1

Comparison of 'PremP009' to 'PremP109'

| Characteristics in which 'PremP009' differs from 'PremP109' | 'PremP109' | 'PremP009' |
|---|---|---|
| Skin Color | Mid Red | Bright Mid to Dark Red |
| Harvest Maturity | Mid to Late Season | Mid to Late Season |
| Amount of Overcolor | Medium | High |
| Shape | Round | Pyriform |
| Postharvest Storage | 10 Weeks | 6-10 Weeks |
| Flavor Profile | European and Nashi flavor | European and Nashi flavor |
| Flowering Time | Mid to Late Season | Late Season |

Asexual propagation by budding was first carried out in Nelson, New Zealand. The variety has since been observed over a number of asexually propagated generations, and has been found to remain true to type.

DETAILED BOTANICAL DESCRIPTION OF THE VARIETY

The following detailed botanical description is based on observations of four-year-old trees made during the 2013 growing season at Havelock North, New Zealand. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor*.—Moderate.
- *Habit*.—Upright.
- *Size*.—Height 3.5 m, spread 2.75 m.
- *Trunk*.—Diameter at 5 cm above graft union 96 mm.
- *Bark texture*.—Smooth with raised lenticels.
- *Bark color*.—Brown 200B.
- *Lenticel color*.—Grey 201B.
- *Lenticel shape*.—Elongated.
- *Lenticel size*.—3 mm×5 mm.
- *Lenticel density*.—About 2 per $cm^2$.

Branch:
- *Size*.—Length 1.75 m; Diameter 23 mm at 1.37 m above graft union.
- *Crotch angle*.—50°; smooth.
- *Branch color*.—200B.
- *Lenticel density*.—2-3 per square cm.
- *Lenticel size*.—Length 2 mm, Height 5 mm.

Dormant one-year-old shoot:
- *Size*.—Diameter 3-5 mm; Length 30-35 mm; Internode length 30 mm.
- *Texture*.—Smooth.
- *Color*.—200A.
- *Lenticels*.—Quantity 2-3 per $cm^2$, color grey-brown 199C, length 2 mm, width 1 mm.

Flower buds:
- *Quantity per spur*.—6 to 10.
- *Shape*.—Round.
- *Length*.—10 mm, diameter 7 to 8 mm.
- *Color*.—Red-purple N63A.

Flowers:
- *Time of flowering*.—Very late.
- *Bloom period*.—First bloom October 8, full bloom October 23 in Hawkes Bay, New Zealand.
- *Quantity per cluster*.—6 to 10.
- *Diameter of fully open flower*.—26 mm to 28 mm.
- *Depth of open flower*.—11 mm to 12 mm.
- *Fragrance*.—Weak.

Petals:
- *Quantity per flower*.—5.
- *Size*.—Length 14 mm, width 9 mm to 10 mm.
- *Shape*.—Ovate with acuminate tip and rounded base.
- *Margin*.—Serrulate.
- *Color*.—Upper surface red-purple 63B, lower surface white.
- *Texture*.—Upper and lower surfaces smooth.

Reproductive organs:
- *Anthers*.—28 to 35 per flower, 1 mm.
- *Stigma*.—Length 1 mm, color yellow-green 153A.
- *Style*.—Length 8 to 9 mm, color yellow-green 153A.
- *Ovary*.—Color 153A.

Sepals:
- *Quantity*.—5.
- *Color*.—Upper surface yellow-green 153A, lower surface yellow-green 146C.
- *Size*.—Length 5 to 5.5 mm, width 3 to 3.5 mm.
- *Shape*.—Pointed with smooth margin.
- *Texture*.—Upper and lower surfaces smooth.

Leaf:
- *Attitude in relation to shoot*.—Upward.
- *Blade margin*.—Serrated.
- *Size*.—Length 12.2 cm, width 8.1 cm.
- *Shape*.—Elliptic.
- *Apex*.—Acuminate.
- *Base*.—Rounded.
- *Texture*.—Smooth.
- *Color*.—Upper surface yellow-green 146D.
- *Color of lower surface*.—Yellow-green 145C.
- *Apex with petiole*.—2.8 cm.
- *Attitude in relation to shoot*.—45°.
- *Petiole size*.—Length 3 cm, diameter 2 mm.
- *Petiole color*.—Greyed-orange 175A.

Fruit:
- *Size*.—Height 70 mm, Width 60 mm, Weight 185 g to 250 g depending on rootstock and crop density.
- *Shape*.—Pyriform.
- *Quantity per cluster*.—3-5.
- *Depth of eye basin*.—10 mm.
- *Width of eye basin*.—17 mm.
- *Length of stalk*.—28 mm; Thickness of stalk 3 mm.
- *Size of lenticels*.—Small 0.25 mm.
- *Greasiness of skin*.—Slight; Color of skin Grey Purple Group 187 B.
- *Intensity of overcolor*.—Medium at harvest, bright at post storage.
- *Skin texture*.—Smooth with 20 or more round lenticels per $cm^2$.
- *Flesh texture*.—Fine, crisp, moderately firm.
- *Juiciness*.—Moderate; Brix 13-14°.
- *Flesh color*.—White 155D.
- *Aroma*.—Average.
- *Stem color*.—Brown 200A.
- *Seeds*.—Quantity per fruit 8-12, quantity per locule 2 to 3, elongated with pointed tip, length 10 mm, width 4 mm.
- *Seed color*.—Brown 200B.
- *Locules*.—4 per fruit, length 6 mm, width 12 mm.

Harvest:
- *Amount of fruit produced per tree per harvest*.—56 fruits (about 10 to 14 kg) at $5^{th}$ leaf.
- *Harvest date range*.—February $25^{th}$ at Hawkes Bay, NZ.

Disease resistance/susceptibility: Resistant to pear scab; Moderately susceptible to fire blight.

Winter hardiness: Hardy in area tested.

Chilling requirement: Winter dormancy required.

Storage: Excellent storage performance at 10 weeks; 14 days ambient shelf life.

Use: Fresh Market.

I claim:

1. A new and distinct pear tree substantially as illustrated and described herein.

* * * * *